US012778903B2

(12) United States Patent
Zou et al.

(10) Patent No.: US 12,778,903 B2
(45) Date of Patent: Nov. 3, 2026

(54) PHARMACEUTICAL COMPOSITION AND BREXPIPRAZOLE ORALLY SOLUABLE FILM

(71) Applicants: WISDOM PHARMACEUTICAL CO., LTD., Nantong (CN); WISDOM PHARMACEUTICAL CO., LTD. GUANGZHOU BRANCH, Guangzhou (CN)

(72) Inventors: Ping Zou, Nantong (CN); Yiguang Qi, Guangzhou (CN); Ni Wang, Guangzhou (CN); Dingchang Ma, Guangzhou (CN)

(73) Assignees: WISDOM PHARMACEUTICAL CO., LTD., Nantong (CN); WISDOM PHARMACEUTICAL CO., LTD. GUANGZHOU BRANCH, Guangzhou (CN)

( * ) Notice: Subject to any disclaimer, the term of this patent is extended or adjusted under 35 U.S.C. 154(b) by 261 days.

(21) Appl. No.: 18/571,222

(22) PCT Filed: Dec. 21, 2022

(86) PCT No.: PCT/CN2022/140816

§ 371 (c)(1),
(2) Date: Dec. 16, 2023

(87) PCT Pub. No.: WO2023/240971

PCT Pub. Date: Dec. 21, 2023

(65) Prior Publication Data

US 2025/0090476 A1 Mar. 20, 2025

(30) Foreign Application Priority Data

Jun. 16, 2022 (CN) ........................ 202210682418.X

(51) Int. Cl.

| | |
|---|---|
| ***A61K 31/496*** | (2006.01) |
| ***A61K 9/70*** | (2006.01) |
| ***A61K 47/10*** | (2017.01) |
| ***A61K 47/14*** | (2017.01) |
| ***A61K 47/32*** | (2006.01) |
| ***A61K 47/38*** | (2006.01) |

(52) U.S. Cl.

CPC .......... *A61K 9/7007* (2013.01); *A61K 31/496* (2013.01); *A61K 47/10* (2013.01); *A61K 47/14* (2013.01); *A61K 47/32* (2013.01); *A61K 47/38* (2013.01)

(58) Field of Classification Search

CPC ............................ A61K 9/7007; A61K 31/496
See application file for complete search history.

(56) References Cited

U.S. PATENT DOCUMENTS

2017/0182105 A1* 6/2017 Krekeler ................ A61K 47/38
2019/0389847 A1 12/2019 Krekeler et al.

FOREIGN PATENT DOCUMENTS

| | | | | |
|---|---|---|---|---|
| CN | 104470499 A | | 3/2015 | |
| CN | 105106142 A | | 12/2015 | |
| CN | 105395528 A | | 3/2016 | |
| CN | 111991373 A | | 11/2020 | |
| CN | 113082004 A | | 7/2021 | |
| CN | 114767663 A | * | 7/2022 | ............. A61K 47/42 |
| CN | 115192549 A | | 10/2022 | |
| JP | 2013253038 A | * | 12/2013 | |

OTHER PUBLICATIONS https://www.cambridge.org/core/journals/cns-spectrums/article/mechanism-of-action-of-brexpiprazole-comparison-with-aripiprazole/410BABD1B670F753928441063F16D61B (Year: 2016).*
https://www.clinpgx.org/pathway/PA166293181#:~:text=Brexpiprazole%20(OPC%2D34712%2C%20IUPAC,%5BArticles%3A40157325%2C%2028750151%2C (Year: 2025).*
https://www.cambridge.org/core/journals/cns-spectrums/article/mechanism-of-action-of-brexpiprazole-comparison-with-aripiprazole/410BABD1B670F753928441063F16D61B (Year: 2018).*
Machine translation for JP 2013253038 A (Year: 2013).*
Machine translation for CN 114767663 A (Year: 2022).*
https://www.xyzchemical.com/what-are-the-examples-of-film-forming-agents/#:~:text=Film%2Dforming%20agents%20are%20not,Controlled%20release%20of%20active%20ingredients. (Year: 2026).*
Wu B, Wu L, He Y, Yin Z, Deng L. Engineered PLGA microspheres for extended release of brexpiprazole: in vitro and in vivo studies. Drug Dev Ind Pharm. Jun. 2021;47(6):1001-1010. doi: 10.1080/03639045.2021.1934859. Epub Aug. 6, 2021. PMID: 34032181.
Jiang Wenfeng et al. R esearch status of brexpiprazole. New Drugs Introduction, vol. 35(13), Jul. 31, 2019. pp. 1402-1405. DOI: 10.13699 /j.cnki.1001-6821.2019.13.024.
PCT International Search Report for International Application No. PCT/CN2022/140816, dated Mar. 8, 2023.

* cited by examiner

*Primary Examiner* — Andrew S Rosenthal
*Assistant Examiner* — Danielle Kim
(74) *Attorney, Agent, or Firm* — MH2 Technology Law Group LLP

(57) ABSTRACT

The present invention discloses a pharmaceutical composition and a brexpiprazole oral soluble film. The pharmaceutical composition comprises brexpiprazole, a film-forming material and a plasticizer, wherein $D_{90}$ of brexpiprazole is: 25 μm≤$D_{90}$≤50 μm. The pharmaceutical composition provided by the present invention can achieve a better dissolution rate with the same efficacy and safety as the reference tablet. Meanwhile, the brexpiprazole oral soluble film provided by the present invention has the advantages of improving the uniformity of API content, controllable dissolution rate, simple preparation process and simple preparation materials.

11 Claims, No Drawings

PHARMACEUTICAL COMPOSITION AND BREXPIPRAZOLE ORALLY SOLUABLE FILM

CROSS-REFERENCE TO RELATED APPLICATIONS

This application is a National Phase of PCT Patent Application No. PCT/CN2022/140816 having International filing date of Dec. 21, 2022, which claims priority of Chinese patent application No. CN202210682418.X, filed on Jun. 16, 2022, and titled "Pharmaceutical composition and brexpiprazole oral soluble film", the contents of which are incorporated herein by reference in its entirety.

TECHNICAL FIELD

The invention relates to a pharmaceutical composition and also to a brexpiprazole oral soluble film.

BACKGROUND OF THE INVENTION

Brexpiprazole tablets were jointly developed by Otsuka Pharmaceutical Co., Ltd. in Japan and Lundbeck Pharmaceutical Co., Ltd. in Denmark to treat schizophrenia and severe depression disorder, and were approved by the FDA for marketing in July 2015. The dosage forms are tablets, with specifications of 0.25 mg, 0.5 mg, 1 mg, 2 mg, 3 mg and 4 mg, under the brand name REXULTI. Brexpiprazole has a molecular formula of $C_{25}H_{27}N_3O_2S$, molecular weight of 433.57, and the structural formula as follows:

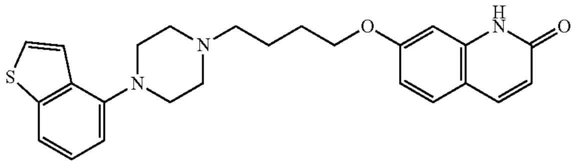 [SMILES: O=c1ccc2ccc(OCCCCN3CCN(c4cccc5sccc45)CC3)cc2[nH]1]

In clinical nursing work, hospitalized psychiatric patients are prone to refusal to take medication during treatment, manifested as direct refusal, concealment of medication, pretending to take medication (including pretending to take medication under the tongue or in the mouth, and spitting it out when the staff is not paying attention) and so on, which results in the disease not achieving the expected treatment effect. Moreover, the incidence of refusal to take medication among patients who have been hospitalized for less than 2 weeks is 90%.

Oral soluble film is a new type of oral administration dosage form at home and abroad in recent years. The way of taking it is to put the oral soluble film on the tongue, which is usually melted completely within 30 seconds and then swallowed with saliva. Its advantages are that it is not easy to spit out due to being adhered to the mouth after administration, dissolved quickly, and can solve the clinical needs which cannot be met with the existing dosage forms. The oral soluble film can be conducive to the control of concealment of medicine behavior in psychiatric patients, and is beneficial to improving patient compliance and indirectly improving the treatment effect.

Brexpiprazole is a white or off-white crystalline powder, which belongs to BCS 2, with low solubility and high permeability, and thus the dissolution rate of the drug is the main reason affecting its bioavailability.

CN105395528A discloses a brexpiprazole oral fast dissolving film and a preparation method thereof. The oral soluble film dissolves slowly, about 50% in 60 minutes. The oral soluble film has soft texture and is easy to deform by pulling, and thus it is difficult to industrialization. JP2013253038A discloses a brexpiprazole oral soluble film and its preparation method. The brexpiprazole oral soluble film comprises a large number of excipients and is a bilayer film, with a complex preparation process and a high production cost.

SUMMARY OF THE INVENTION

In view of the problems existing in the prior art, the present invention provides a brexpiprazole oral soluble film and a preparation method thereof, which have the advantages of improved uniformity of API (Active pharmaceutical ingredient) content, controllable dissolution rate, simple preparation process and simple preparation excipients.

In order to realize the purpose of the present invention, the following technical solution is adopted.

In a first aspect, the present invention provides a pharmaceutical composition comprising brexpiprazole, a film-forming material and a plasticizer, wherein $D_{90}$ of brexpiprazole is 25 $\mu m \leq D_{90} \leq 50$ μm.

The present invention unexpectedly discovered that controlling the particle size of brexpiprazole within a certain range can achieve a controllable dissolution rate and a good reproducibility, making it has the same therapeutic effect and safety as reference tablets. Meanwhile, brexpiprazole oral film with controlled particle size of brexpiprazole can achieve the same dissolution rate as that of the reference tablets and improve patient compliance. The brexpiprazole oral soluble film can absorb drugs through the oral mucosa and exert systemic effects. In some embodiments, the $D_{90}$ of brexpiprazole is 25 μm, 25.7 μm, 27.5 μm, 30 μm, 30.3 μm, 32.5 μm, 35 μm, 37.1 μm, 37.5 μm, 40 μm, 42.5 μm, 45 μm, 47.5 μm, 48.4 μm, or 50 μm. In some embodiments, the $D_{90}$ of brexpiprazole ranges from 25 μm to 40 μm. In the present invention, when the particle size $D_{90}$ of brexpiprazole is controlled between 25 μm and 50 μm, the dissolution is stable and controllable, the dissolution difference at the same time point is not more than 10%, and the oral soluble film can achieve a bioavailability bioequivalent to that of the reference tablets. When the particle size $D_{90}$ of brexpiprazole is below 25 μm, the dissolution rate would be too fast to control. When the dissolution rate is too fast, the blood concentration in the body may fluctuate significantly. When the particle size $D_{90}$ of brexpiprazole is above 50 μm, the dissolution rate would be slowly. In some embodiments, the D90 of brexpiprazole is: 30 $\mu m \leq D_{90} \leq 50$ μm. In some embodiments, the D90 of brexpiprazole is: 30 $\mu m < D_{90} \leq 50$ μm. In some embodiments, the D90 of brexpiprazole is: 30 $\mu m < D_{90} < 50$ μm. In some embodiments, the D90 of brexpiprazole is: 30.3 $\mu m \leq D_{90} \leq 50$ μm.

In some embodiments, the plasticizer is selected from one or more of polyethylene glycol, glycerin, triethyl citrate, or polysorbate. In some embodiments, the plasticizer is polysorbate 80, polyethylene glycol 400, or other polyethylene glycol that can be used as the plasticizer (e.g., polyethylene glycol 600, polyethylene glycol 800, polyethylene glycol 1000, polyethylene glycol 1500, polyethylene glycol 4000, or polyethylene glycol 6000).

In some embodiments, the film-forming material is selected from one or more of povidone, copovidone, hydroxypropyl methylcellulose, hydroxypropyl cellulose, hydroxyethyl cellulose, polyvinyl alcohol, sodium carboxymethyl cellulose, pectin, guar gum, pullulan, sodium alginate, chitosan, polyvinyl alcohol-polyethylene glycol copolymer, or xanthan gum. In some embodiments, the film-forming material is povidone K29/32, copovidone VA64, hydroxypropyl methylcellulose E5, hydroxypropyl methylcellulose E15, hydroxypropyl methylcellulose E50, or hydroxypropyl cellulose SSL, or the like.

In some embodiments, the mass percent content of brexpiprazole in the pharmaceutical composition is 2% to 40%. In some embodiments, the mass percent content of brexpiprazole in the pharmaceutical composition is 2% to 24%. In some embodiments, the mass percent content of brexpiprazole in the pharmaceutical composition is 3% to 20%. In some embodiments, the mass percent content of brexpiprazole in the pharmaceutical composition is 2%, 3%, 5%, 7.5%, 10%, 12.5%, 15%, 17.5%, 20%, 25%, 30%, 35%, or 40%. In the present invention, controlling the mass content of brexpiprazole within the above range, especially within 3% to 20% stable and controllable dissolution of the prepared formulation can be achieved.

In some embodiments, the ratio of the mass of brexpiprazole to the total mass of the film-forming material and the plasticizer is 1:(2 to 50). In some embodiments, the ratio of the mass of brexpiprazole to the total mass of the film-forming material and the plasticizer is 1:(4 to 35). In some embodiments, the ratio of the mass of brexpiprazole to the total mass of the film-forming material and the plasticizer is 1:2, 1:4, 1:6, 1:8, 1:10, 1:15, 1:20, 1:25, 1:30, 1:35, 1:40, 1:45, or 1:50. In the present invention, controlling the mass of brexpiprazole and the total mass of the film-forming material and the plasticizer within the above range, stable and controllable dissolution of the formulation can be achieved.

In some embodiments, a ratio of the mass of the film-forming material to the mass of the plasticizer is (2 to 50): 1. In some embodiments, the ratio of the mass of the film-forming material to the mass of the plasticizer is (5 to 20):1. In some examples, the ratio of the mass of the film-forming material to the mass of the plasticizer is 2:1, 5:1, 10:1, 15:1, 20:1, 25:1, 30:1, 35:1, 40:1, 45:1, or 50:1.

In some embodiments, the pharmaceutical composition comprises or consists of the following components: 2 parts by weight of brexpiprazole; 5 to 80 parts (e.g., 5, 6, 8, 10, 12, 15, 20, 30, 40, 50, 60, 70, or 80, etc.) by weight of the film-forming material; 0.2 to 10 (e.g., 0.2, 0.5, 1, 1.5, 2, 3, 4, 5, 6, 7, 8, 9, 10, etc.) parts by weight of the plasticizer.

In some embodiments, the pharmaceutical composition comprises or consists of the following components: 2 parts by weight of brexpiprazole; 5 to 60 (e.g., 5, 6, 8, 10, 12, 15, 20, 30, 40, 50, or 60, etc.) parts by weight of the film-forming material; 0.5 to 10 (e.g., 0.5, 1, 1.5, 2, 3, 4, 5, 6, 7, 8, 9, 10, etc.) parts by weight of the plasticizer.

In a second aspect, the present invention provides a pharmaceutical suspension comprising the pharmaceutical composition as described in the first aspect of the present invention, and water.

In some embodiments, the pharmaceutical suspension has a viscosity greater than 3,500 mPa·s. In some embodiments, the viscosity of the pharmaceutical suspension is in a range from 3,500 to 15,000 mPa·s. In some embodiments, the viscosity of the pharmaceutical suspension is in a range from 3,500 to 10,000 mPa·s. In some embodiments, the viscosity of the pharmaceutical suspension is 3,500 mPa·s, 4,000 mPa·s, 5,000 mPa·s, 6,000 mPa·s, 7,000 mPa·s, 8,000 mPa·s, 9,000 mPa·s, 10,000 mPa·s, 11,000 mPa·s, 12,000 mPa·s, 13,000 mPa·s, 14,000 mPa·s, or 15,000 mPa·s. The inventor found that when the viscosity of the pharmaceutical suspension is ≥3,500 mPa·s, preferred viscosity range being from 3,500 mPa·s to 15,000 mPa·s, the uniformity of API content can be good after deaeration; further preferred viscosity range is in a range from 3,500 mPa·s to 10,000 mPa·s, and when the viscosity of the pharmaceutical suspension is within this range, the uniformity of API content can meet the standard without stratification.

In some embodiments, the $D_{90}$ of brexpiprazole in the pharmaceutical suspension is 25 μm to 50 μm. In some embodiments, the $D_{90}$ of brexpiprazole in the pharmaceutical suspension is 25 μm to 40 μm. In some embodiments, the $D_{90}$ of brexpiprazole in the pharmaceutical suspension is 25 μm, 27.5 μm, 30 μm, 32.5 μm, 35 μm, 37.5 μm, 40 μm, 42.5 μm, 45 μm, 47.5 μm, or 50 μm.

In some embodiments, the pharmaceutical suspension comprises or consists of the following components: 2 parts by weight of brexpiprazole; 5 to 80 (e.g., 5, 6, 8, 10, 12, 15, 20, 30, 40, 50, 60, 70, or 80, etc.) parts by weight of the film-forming material; 0.2 to 10 (e.g., 0.2, 0.5, 1, 1.5, 2, 3, 4, 5, 6, 7, 8, 9, 10, etc.) parts by weight of the plasticizer; and 50 to 150 (e.g., 50, 60, 70, 80, 90, 100, 110, 120, 130, 140, or 150, etc.) parts by weight of water.

In some embodiments, the pharmaceutical suspension comprises or consists of the following components: 2 parts of brexpiprazole by weight, 5 to 60 (e.g., 5, 6, 8, 10, 12, 15, 20, 30, 40, 50, or 60, etc.) parts of the film-forming material, 0.5 to 10 (e.g., 0.5, 1, 1.5, 2, 3, 4, 5, 6, 7, 8, 9, 10, etc.) parts of the plasticizer; and 60 to 120 (e.g., 60, 70, 80, 90, 100, 110, 120, etc.) parts of water by weight.

In a third aspect, the present invention provides a brexpiprazole oral soluble film comprising a pharmaceutical composition described in the first aspect of the present invention or prepared by the pharmaceutical suspension described in the second aspect of the present invention as a raw material.

In a fourth aspect, the present invention provides a preparation method of a brexpiprazole oral soluble film described in the third aspect, comprising steps of:

(1) dispersing brexpiprazole in water, adding and mixing a film-forming material and a plasticizer to obtain a pharmaceutical suspension;

(2) subjecting the pharmaceutical suspension to a deaeration treatment; and (3) preparing the film with the pharmaceutical suspension obtained in step (2).

In some embodiments, in step (1), brexpiprazole is dispersed in water by high-speed homogenization for 15 to 60 (e.g., 15, 20, 25, 30, 35, 40, 45, 55, or 60, etc.) minutes.

In some embodiments, in step (1), the film-forming material and the plasticizer are added for mixing 15 to 60 (e.g., 15, 20, 25, 30, 35, 40, 45, 50, 55, or 60, etc.) minutes.

In some embodiments, in step (2), the deaeration treatment is carried out by using a vacuum deaerator.

In some embodiments, in step (2), the vacuum deaerator can be a vacuum centrifugal deaerator or a vacuum oven.

In some embodiments, in step (3), the film is prepared at a temperature in a range from 50 to 80° C. In some embodiments, the film is prepared at a temperature of 50° C., 55° C., 60° C., 65° C., 70° C., 75° C., or 80° C.

In some embodiments, the preparation method comprises the following steps of: adding brexpiprazole to a purified water with high-speed homogenization for 30 minutes; then transferring the homogenized sample to a stirring equipment and starting the stirring equipment; adding a film material and a plasticizer to the resulting sample and stirring for 30 minutes to obtain a suspension; then subjecting the suspension to a deaeration treatment by using a vacuum centrifugal deaerator; spreading the suspension on a coating machine, fixing, adjusting a scraper to zero, and setting the heating temperature at 50 to 80° C. for coating, to obtain the brexpiprazole oral soluble film.

By controlling the particle size of the active pharmaceutical ingredient (API) in the brexpiprazole oral soluble film, the invention can achieve a dissolution rate with good controllability and reproducible in the gastrointestinal tract, and achieves the equivalent bioavailability with the reference tablets. By controlling the viscosity of the coating suspension, the present invention can meet the standard for the uniformity of API content, and no content stratification occurs. The brexpiprazole oral soluble film of the present invention has good stability and palatability. When the brexpiprazole oral soluble film of the present invention is used, the brexpiprazole oral soluble film is placed on the tongue of the mouth, and after the film is dissolved, the drug is absorbed into the gastrointestinal tract with the saliva.

EMBODIMENTS

In order to render the purposes, technical solutions, and advantages of the present invention clearer, the present disclosure will be further described in detail below in combination with examples. The specific examples described herein are only used to explain the present invention but not to constitute any limitation to the present invention.

Test Method

Dissolution Method:

The sample is took according to USP IV, paddle-plate method, with a dissolution medium of 0.1 M hydrochloric acid solution, a rotational speed of 50 rpm, and a sampling time of 5 minutes/15 minutes/30 minutes. After sampling, HPLC is used for dissolution rate detection. Except for the reference formulation, this analysis method is used for detection and analysis in the following text, and the dissolution results are expressed as means (N=3).

Viscosity Detection:

Testing with rotary digital viscometer (Provided by Lichen), an appropriate amount of flowable sample is took and placed in a beaker. No 3 rotor is rotated at 1000 rpm revolutions per minute, immersed vertically in the center of the sample to make the liquid level reach the rotating liquid level mark. The sample and the rotor are kept in the test vessel at a constant temperature of 25±0.5° C., and the sample temperature is controlled uniformly. Rotating is started and the value is read when it stabilized, to obtain the sample viscosity value, with a unit of centipores (mPa·s).

Particle Size Detection:

A Malvern laser particle size analyzer MS3000 is used for particle size detection, and water is used as a dispersant. The sample is tested according to the equipment operating procedures. The stirring speed is set to 500 rpm, and the measurement frequency is 3 times. After confirming that the stirring is in working mode, the start button is pressed, the instrument is initialized, and the light is automatically aligned. After the background measurement is completed, the sample is manually added until the shading reaches the range, and the Start button is pressed to measure. Finally, the measurement data $D_{90}$ is obtained, "$D_{90}$" refers to a particle size value that 90% of particles with a particle size lower than the stated value. For example, $D_{90}$:9.6 μm refers to 90% of particles with a particle size below 9.6 μm, μm referring to micrometers.

Comparative Example 1 Dissolution Test of Reference Formulation (Brexpiprazole Tablets)

Brexpiprazole tablets (REXULTI, 2 mg, batch number: BMS05420A, manufacturer: Otsuka Pharmaceutical Co., Ltd.) were dissolved in 0.1 M hydrochloric acid solution. Dissolution method: according to USP II, paddle method, 0.1 M hydrochloric acid solution was used as a dissolution medium, with a rotational speed of 50 rpm and sampling times of 5 min, 15 min, and 30 min. After sampling, HPLC was used for release detection. The results are shown in the Table 1.

TABLE 1

| Sample batch number | 5 min | 15 min | 30 min |
|---|---|---|---|
| BMS05420A | 31% | 48% | 60% |

Comparative Example 2 Investigation on Different pH Values when the $D_{90}$ of Brexpiprazole is 3.96 μm Preparation process: Brexpiprazole according to each of the formulations was slowly added to purified water, with high-speed homogenization for 30 minutes. The sample was then transferred to a stirring equipment, which was turned on. Hypromellose and polyethylene glycol were slowly added to the stirring equipment and stirred for 30 minutes. Then, the pH of a coating suspension of formulation 1 was measured and recorded. The coating suspensions of formulation 2, formulation 3 and formulation 4 were added with 0.1M of sodium bicarbonate solution to adjust the pH to 8.30, 10.41 and 12.13, respectively. Next, the prepared coating suspensions were deaerated by a vacuum centrifugal deaerator, and detected for viscosity. Then, the substrate was laid on a coating machine and fixed. The scraper was adjusted to zero, and the heating temperature was set at 50 to 80° C. for performing the coating. After the coating was finished, the sample was cut to a certain size, and tested for dissolution. The component dosages of the formulations are shown below in Table 2.

TABLE 2

| Name | Formulation 1 (mg) | Formulation 2 (mg) | Formulation 3 (mg) | Formulation 4 (mg) | Note |
|---|---|---|---|---|---|
| Brexpiprazole $D_{90}$ = 3.96 μm | 2.00 | 2.00 | 2.00 | 2.00 | active ingredient |
| Hypromellose | 20.00 | 20.00 | 20.00 | 20.00 | film-forming material |
| Polyethylene glycol | 1.00 | 1.00 | 1.00 | 1.00 | plasticizer |
| Sodium bicarbonate | without | with | with adjustment | with adjustment | pH regulator |

TABLE 2-continued

| Name | Formulation 1 (mg) | Formulation 2 (mg) | Formulation 3 (mg) | Formulation 4 (mg) | Note |
|---|---|---|---|---|---|
| | adjustment to pH, pH 6.66 | adjustment to pH 8.30 | to pH 10.41 | to pH 12.13 | |
| Purified water | 85.26 | 85.26 | 85.26 | 85.26 | solvent |
| Viscosity (mPa · s) | 5,429 | 5,475 | 6,412 | 5,876 | N/A |

Note:
Water was removed during the process and not included in the product weight.

The results of dissolution of the samples which were prepared according to the above formulations in 0.1 M hydrochloric acid are shown in Table 3.

TABLE 3

| Sample batch number | 5 min | 15 min | 30 min |
|---|---|---|---|
| Formulation 1 | 65% | 92% | 95% |
| Formulation 2 | 52% | 86% | 96% |
| Formulation 3 | 58% | 91% | 99% |
| Formulation 4 | 65% | 90% | 98% |

The results showed that when the $D_{90}$ of brexpiprazole was 3.96 μm, the films coated with different pH in the range from 6.66 to 12.13 were dissolved rapidly, and the dissolutions were more than 85% in 15 min. The dissolutions were faster than the reference tablets, which could lead to rapid absorption and excessive fluctuation of blood drug concentration in patients, causing adverse reactions.

Comparative Example 3 Investigation on Different Film-Forming Materials when the $D_{90}$ of Brexpiprazole is 3.96 μm Preparation process: Brexpiprazole according to each of the formulations was slowly added to purified water, with high-speed homogenization for 30 minutes. The sample was then transferred to a stirring equipment, which was turned on. Hypromellose and polyethylene glycol were slowly added to the stirring equipment and stirred for 30 minutes. Next, the prepared coating suspensions were deaerated by a vacuum centrifugal deaerator, and detected for viscosity. Then, a substrate was laid on a coating machine and fixed. The scraper was adjusted to zero, and the heating temperature was set at 50 to 80° C. for performing the coating. After the coating was finished, the sample was cut to a certain size, and tested for dissolution. The component dosages of the formulations are shown below in Table 4.

TABLE 4

| Name | Formulation 1 (mg) | Formulation 4 (mg) | Formulation 5 (mg) | Note |
|---|---|---|---|---|
| Brexpiprazole $D_{90}$ = 3.96 μm | 2.00 | 2.00 | 2.00 | active ingredient |
| Hypromellose E5LV | 20.00 | N/A | N/A | film-forming material |
| Hypromellose E15 | N/A | 20.00 | N/A | film-forming material |
| Hypromellose E50LV | N/A | N/A | 20.00 | film-forming material |
| Polyethylene glycol | 1.00 | 1.00 | 1.00 | plasticizer |
| Purified water | 82.56 | 82.56 | 82.56 | solvent |
| Viscosity (mPa · s) | 4,843 | 5,921 | 6,980 | N/A |

Note:
Water was removed during the process and not included in the product weight.

The results of dissolution of the samples which were prepared according to the above formulations in 0.1 M hydrochloric acid are shown in Table 5.

TABLE 5

| Sample batch number | 5 min | 15 min | 30 min |
|---|---|---|---|
| Formulation 1 | 65% | 92% | 95% |
| Formulation 4 | 46% | 86% | 95% |
| Formulation 5 | 21% | 85% | 96% |

When the $D_{90}$ of brexpiprazole was 3.96 μm, the prepared pharmaceutical suspensions with different types of the film-forming materials were coated according to the above preparation process, cut to the certain shape, and detected for dissolution. The results showed that the coated drug film dissolved quickly, more than 85% in 15 min, which would lead to too fast absorption in the body and cause large fluctuation of blood drug concentration.

Comparative Example 4 Dissolution of Oral Soluble Film Prepared by Reference to Preparation Process Formulation 6: First, formulation amounts of acesulfame, glycerol, polyethylene glycol, hypromellose, and polysorbate 80 were added to an aqueous solution. After stirring and dissolution, gelatin and Xanthan gum were added to the resulting mixture, which was fully dissolved at 60-70° C. water bath to obtain a gelatin blank glue liquid. Then brexpiprazole was added and stirred dispersed uniformly to obtain the brexpiprazole glue solution, and then stirring deaerated under vacuum condition. After deaerating, the brexpiprazole glue solution was coated evenly to the substrate with a scraper, and heated to 70-80° C. for drying, cut into a certain size, to obtain the brexpiprazole oral soluble film. The brexpiprazole oral soluble film was tested for dissolution.

Formulation 7: First, the above amounts of acesulfame, glycerol and polysorbate were added to the aqueous solution. After stirring and dissolution, gelatin was added. The resulting mixture was heated at a 60-70° C. water bath for fully dissolving to obtain a gelatin blank glue liquid. Brexpiprazole was added and stirred uniformly to obtain the brexpiprazole glue solution. The brexpiprazole glue solution was deaerated with stirring under vacuum. After the deaerating, the mixture was coated to the substrate with a scraper, heated to 70-80° C. and dried, cut into a certain size, to obtain the brexpiprazole oral soluble film. The brexpiprazole oral soluble film was tested for dissolution.

The component dosages of the formulations are shown below in Table 6.

TABLE 6

| Name | Weight of formulation 6 (g) | Weight of formulation 7 (g) |
|---|---|---|
| Brexpiprazole $D_{90}$ = 37.1 μm | 4.00 | 4.00 |
| Gelatin | 5.00 | 5.00 |
| Hypromellose | 1.00 | N/A |
| Xanthan gum | N/A | 1.00 |
| Glycerol | 2.00 | 2.00 |
| Polysorbate 80 | 1.00 | 1.00 |
| Acesulfame | 5.00 | 5.00 |
| Polyethylene glycol | 1.00 | N/A |
| Purified water | 15.00 | 15.00 |

The dissolution results of the samples prepared by the formulations described above in 0.1 M hydrochloric acid are shown below in Table 7.

TABLE 7

| Sample batch number | 5 min | 15 min | 30 min |
|---|---|---|---|
| Formulation 6 | 26% | 29% | 32% |
| Formulation 7 | 39% | 43% | 47% |

The results showed that the dissolution of formulation 6 and formulation 7 were slow, less than 50% in 30 min; and the prepared soluble film was soft and easy to deform during the pulling process, and thus the industrial production is difficult.

Comparative Example 5 Dissolution of Oral Soluble Film Prepared by Reference to JP2013253038A Preparation process: (1) Formulation amounts of hypromellose, maltitol, sucralose and polyethylene glycol were added to the aqueous solution. After stirring and dissolution, titanium dioxide was added and stirred uniformly to obtain a support layer suspension. The support layer suspension was deaerated under vacuum. The support layer suspension was coated uniformly to the substrate with a scraper, heated to 70-80° C. for drying; (2) Formulation amounts of HPC SSL, maltitol, sucralose and flavor were added to the aqueous solution, after stirring and dissolution, brexpiprazole was added and stirred uniformly to obtain a drug layer suspension. The drug layer suspension was deaerated under vacuum. The drug layer suspension was evenly coated onto the support layer with a scraper, heated to 70-80° C. for drying, and cut into a certain size, to obtain a brexpiprazole oral soluble film. The oral soluble film was tested for dissolution. The component dosages of the formulation are shown below in Table 8.

TABLE 8

| Content | Name | Formulation 8 | Formulation 9 |
|---|---|---|---|
| Content | Component | Unit dose (mg) | |
| Support layer | Titanium dioxide | 0.80 | 0.80 |
| | Hypromellose | 4.38 | 4.38 |
| | Maltitol | 2.40 | 2.40 |
| | Sucralose | 0.02 | 0.02 |
| | Polyethylene glycol | 0.40 | 0.40 |
| | Purified water | 23.75 | 23.75 |
| Content | Component/drug substance particle size | Unit dose(mg) | |
| Drug layer | Brexpiprazole | 0.50 $D_{90}$ = 9.6 μm | 0.50 $D_{90}$ = 60.8 μm |
| | HPC SSL | 7.60 | 7.60 |
| | Maltitol | 3.37 | 3.37 |
| | Sucralose | 0.03 | 0.03 |
| | Flavor | 0.01 | 0.01 |
| | Purified water | 37.50 | 37.50 |
| | Total | 19.60 | 19.60 |

Note:
Water was removed during the process and not included in the product weight.

The dissolution results of the samples prepared by the formulations described above in 0.1 M hydrochloric acid are shown below in Table 9.

TABLE 9

| Sample batch number | 5 min | 15 min | 30 min |
|---|---|---|---|
| Formulation 8 | 40% | 75% | 86% |
| Formulation 9 | 11% | 30% | 38% |

The brexpiprazole oral soluble film disclosed in JP2013253038A were added with a large number of excipients, and prepared as bilayer films. The preparation process is complex, with large dosage of excipients and high cost of process. Under the particle size range of the active ingredients in this patent, there is a significant difference in dissolution rate. The 30 minutes dissolution of brexpiprazole oral soluble film using active ingredient of $D_{90}$ being 9.6 μm was 86%, and the 30 minutes dissolution of brexpiprazole oral soluble film using active ingredient of $D_{90}$ being 60.8 μm was below 50%. Therefore, the dissolution rate was uncontrollable, leading to large differences between the products of different batches, and affecting the quality of the products.

Example 1 Brexpiprazole Oral Soluble Films with Different Material Particles

Preparation process: Brexpiprazole according to each of the formulations was slowly added to purified water, with high-speed homogenization for 30 minutes. The sample was then transferred to a stirring equipment, which was turned on. Hypromellose and polyethylene glycol were slowly added and stirred for 30 minutes. Next, the prepared coating suspensions were deaerated by a vacuum centrifugal deaerator, and detected for viscosity. Then, a substrate was laid on a coating machine and fixed. A scraper was adjusted to zero, and the heating temperature was set at 50 to 80° C. for performing the coating. After the coating was finished, the sample was cut to a certain size, and tested for dissolution. The component dosages of the formulations are shown below in Table 10.

TABLE 10

| Name/ Material particle size | Formulation 10 (mg) $D_{90}$ = 9.6 μm | Formulation 11 (mg) $D_{90}$ = 25.7 μm | Formulation 12 (mg) $D_{90}$ = 30.3 μm | Formulation 13 (mg) $D_{90}$ = 37.1 μm | Formulation 14 (mg) $D_{90}$ = 48.4 μm | Formulation 15 (mg) $D_{90}$ = 60.8 μm | Note N/A |
|---|---|---|---|---|---|---|---|
| Brexpiprazole | 2.00 | 2.00 | 2.00 | 2.00 | 2.00 | 2.00 | active ingredient |
| Hypromellose E5LV | 20.00 | 20.00 | 20.00 | 20.00 | 20.00 | 20.00 | film-forming material |
| Polyethylene glycol 400 | 1.00 | 1.00 | 1.00 | 1.00 | 1.00 | 1.00 | plasticizer |
| Purified water | 82.56 | 82.56 | 82.56 | 82.56 | 82.56 | 82.56 | solvent |
| Viscosity (mPa · s) | 5,230 | 5,310 | 5,100 | 5,430 | 5,256 | 5,320 | N/A |

Note:
Water was removed during the process and not included in the product weight.

The dissolution results of the samples prepared by the formulations described above in 0.1 M hydrochloric acid are shown below in Table 11.

TABLE 11

| Sample batch number/$D_{90}$ | | 5 min | 15 min | 30 min |
|---|---|---|---|---|
| Formulation 10 | 9.6 μm | 42% | 73% | 87% |
| Formulation 11 | 25.7 μm | 34% | 54% | 66% |
| Formulation 12 | 30.3 μm | 32% | 55% | 64% |
| Formulation 13 | 37.1 μm | 31% | 55% | 64% |
| Formulation 14 | 48.4 μm | 27% | 47% | 57% |
| Formulation 15 | 60.8 μm | 11% | 30% | 38% |

The results showed that when the API particle size $D_{90}$ was controlled between 25 μm and 50 μm, the dissolution was stable and controlled, and the dissolution difference at the same time point did not exceed 10%; when the API particle size $D_{90}$ was below 25 μm, the dissolution rate was too fast and uncontrollable, while the dissolution rate was too fast, which would lead to excessive fluctuation of blood concentration in the body. Dissolution was slow when the API particle size $D_{90}$ was above 50 μm.

Example 2 Investigation on Content Uniformity

Preparation process: Brexpiprazole according to formulation 16 was slowly added to purified water, with high-speed homogenization for 30 minutes. The sample was then transferred to a stirring equipment, which was turned on. Hypromellose and polyethylene glycol were slowly added and stirred for 30 minutes. Next, the prepared coating suspension was deaerated by a vacuum drying tank overnight. The pressure of the vacuum drying tank was set to: −0.08 MPa and the temperature was set to 25° C. The usages of the components are shown below in Table 12.

Viscosity detection was performed after deaerating, and the viscosity of formulation 16 was 1,916 mPa·s.

TABLE 12

| formulation 16 | | |
|---|---|---|
| Name | Single dose (mg) | Note |
| Brexpiprazole $D_{90}$ = 37.1 μm | 2.00 | active ingredient |
| Hypromellose E5LV | 20.00 | film-forming material |
| Polyethylene glycol 400 | 1.00 | plasticizer |
| Purified water | 113.3 | solvent |
| Viscosity (mPa · s) | | 1,916 |

Note:
Water was removed during the process and not included in the product weight.

A mixing content uniformity refers to the uniformity of the drug suspension before and after the sample is well mixed and deaerated. In this example, before and after deaerating, three samples were taken from different positions of the mixing tank, including the upper, middle and lower layers, respectively. The brexpiprazole content of each sample was tested and the relative standard deviation (RSD) was calculated. RSD=standard deviation/arithmetic mean of the calculation results. When RSD was ≤3%, it represents that the uniformity of content is good; when RSD was >3%, it represented that the uniformity of content is bad. The mixing content uniformity results are shown below in Table 13.

TABLE 13

| Batch | | Formulation 16 | | |
|---|---|---|---|---|
| Content before deaerating | upper layer | 99.3% | 96.4% | 98.6% |
| | middle layer | 98.4% | 99.2% | 98.2% |
| | lower layer | 100.2% | 99.7% | 100.4% |
| | mean ± RSD | 99.0% ± 1.3% | | |
| Content after deaerating | upper layer | 80.7% | 74.9% | 63.7% |
| | middle layer | 89.8% | 91.5% | 91.3% |
| | lower layer | 109.1% | 126.4% | 125.4% |
| | mean ± RSD | 94.8% ± 22.9% | | |

The results showed that the content uniformity of formulation 16 drug suspension at different positions was good before deaerating, and RSD≤3%, but after deaerating, the sample content uniformity was not ideal with RSD>3%, representing that there was stratification appeared in the drug suspension, low API content in the upper layer, high API content in the lower layer, and drug deposition.

Example 3 Investigations on Content Uniformity

Preparation process: Brexpiprazole according to each of the formulations was slowly added to purified water, with high-speed homogenization for 30 minutes. The sample was then transferred to a stirring equipment, which was turned on. Hypromellose E5LV and polyethylene glycol 400 were slowly added and stirred for 30 minutes. Next, the prepared coating suspension was deaerated by a vacuum centrifugal deaerator. Parameters of the vacuum centrifugal deaerator were set as: stage 1:300 rpm, 1 minute, non-vacuum; stage 2:750 rpm, 1 minute, vacuum degree-0.04 MPa; stage 3:1000 rpm, 2 min, vacuum degree −0.04 MPa; stage 4: rotating speed 700 rpm, 1.5 min, vacuum degree −0.04 MPa; and stage 5: rotating speed 400 rpm, 0.5 min, vacuum degree-0.04 MPa. The usages of the components are shown below in Table 14.

Viscosity was detected after the deaerating, and the viscosity of formulation 16 was 1,920 (mPa·s).

TABLE 14

| Formulation 17 | | |
|---|---|---|
| Name | Single dose(mg) | Note |
| Brexpiprazole $D_{90}$ = 37.1 μm | 2.00 | active ingredient |
| Hypromellose E5LV | 20.00 | film-forming material |
| Polyethylene glycol 400 | 1.00 | plasticizer |
| Purified water | 113.3 | solvent |
| Viscosity (mPa · s) | 1,920 | |

Note:
Water was removed during the process and not included in the product weight.

A mixing content uniformity refers to the uniformity of the drug suspension before and after the sample is well mixed and deaerated. In this example, before and after deaerating, three samples were taken from different positions of the mixing tank, including the upper, middle and lower layers, respectively. The brexpiprazole content of each sample was tested and the relative standard deviation (RSD) was calculated. RSD=standard deviation/arithmetic mean of the calculation results. When RSD was ≤3%, it represents that the uniformity of content is good; when RSD was >3%, it represents that the uniformity of content was bad. The mixing content uniformity results are shown below in Table 15.

TABLE 15

| Batch | | Formulation 17 | | |
|---|---|---|---|---|
| Content before deaerating | upper layer | 102.2% | 100.1% | 97.9% |
| | middle layer | 100.5% | 99.5% | 102.6% |
| | lower layer | 105.0% | 99.7% | 99.5% |
| | mean ± RSD | 100.8% ± 2.2% | | |
| Content after deaerating | upper layer | 82.0% | 82.8% | 87.7% |
| | middle layer | 84.0% | 86.6% | 111.1% |
| | lower layer | 124.9% | 94.9% | 103.9% |
| | mean ± RSD | 95.3% ± 15.8% | | |

The results showed that the content uniformity of formulation 17 drug suspension at different positions was good before deaerating, but after deaerating, the sample content uniformity was not ideal with RSD>3%, representing that there is stratification appeared in the drug suspension, low API content in the upper layer, high API content in the lower layer, and drug deposition.

Example 4 Investigation on Content Uniformity

The preparing process and content uniformity sample were the same as those in Example 3. The deaerating method used a vacuum centrifugal deaerator for deaerating. The dosages of the formulations are shown below in Table 16. The results of content uniformity are as follows in Table 17, Table 18, Table 19 and Table 20.

TABLE 16

| Name | Formulation 18 (mg) | Formulation 19 (mg) | Formulation 20 (mg) | Formulation 21 (mg) | Note |
|---|---|---|---|---|---|
| Brexpiprazole $D_{90}$ = 37.1 μm | 2.00 | 2.00 | 2.00 | 2.00 | active ingredient |
| Hypromellose E5LV | 20.00 | 20.00 | 20.00 | 20.00 | film-forming material |
| Polyethylene glycol 400 | 1.00 | 1.00 | 1.00 | 1.00 | plasticizer |
| Purified water | 90.11 | 86.00 | 80.00 | 60.00 | solvent |
| Viscosity (mP · s) | 2,498 | 3,512 | 8,703 | 14,236 | N/A |

TABLE 17

| Batch | | Formulation 18 | | |
|---|---|---|---|---|
| Content before deaerating | upper layer | 96.7% | 97.2% | 95.6% |
| | middle layer | 98.5% | 94.5% | 95.2% |
| | lower layer | 99.8% | 95.4% | 96.2% |
| | mean ± RSD | 96.6% ± 1.8% | | |
| Content after deaerating | upper layer | 74.6% | 76.5% | 64.0% |
| | middle layer | 81.2% | 82.5% | 81.5% |
| | lower layer | 104.3% | 123.9% | 223.4% |
| | mean ± RSD | 101.3% ± 48.5% | | |

The results showed that the drug suspension of formulation 18 had good sample uniformity at different positions before deaerating, but after deaerating, the sample content uniformity was not ideal with RSD>3%, representing that there was stratification appeared in the drug suspension, low API content in the upper layer, high API content in the lower layer, and drug deposition.

TABLE 18

| Batch | | Formulation 19 | | |
|---|---|---|---|---|
| Content before deaerating | upper layer | 102.5% | 98.5% | 99.8% |
| | middle layer | 103.5% | 99.5% | 100.5% |
| | lower layer | 98.7% | 101.8% | 100.4% |
| | mean ± RSD | 100.6% ± 1.7% | | |
| Content after deaerating | upper layer | 99.4% | 98.3% | 100.0% |
| | middle layer | 98.9% | 99.7% | 98.8% |
| | lower layer | 98.4% | 99.8% | 99.5% |
| | mean ± RSD | 99.2% ± 0.7% | | |

The results showed that the drug suspension of formulation 19 contained uniform samples at different positions before and after deaerating, with RSD<3%.

TABLE 19

| Batch | | Formulation 20 | | |
|---|---|---|---|---|
| Content before deaerating | upper layer | 97.1% | 97.1% | 97.1% |
| | middle layer | 98.4% | 97.6% | 97.0% |
| | lower layer | 97.6% | 98.0% | 98.0% |
| | mean ± RSD | 97.6% ± 0.6% | | |
| Content after deaerating | upper layer | 97.7% | 97.7% | 97.7% |
| | middle layer | 96.3% | 98.0% | 97.5% |
| | lower layer | 99.5% | 99.4% | 99.5% |
| | mean ± RSD | 98.1% ± 1.2% | | |

The results showed that the drug suspension of formulation 20 contained uniform samples at different positions before and after deaerating, with RSD <3%.

TABLE 20

| Batch | | Formulation 21 | | |
|---|---|---|---|---|
| Content before deaerating | upper layer | 99.3% | 99.9% | 99.1% |
| | middle layer | 100.2% | 100.1% | 98.5% |
| | lower layer | 99.5% | 100.3% | 102.0 |
| | mean ± RSD | 99.9% ± 1.0% | | |
| Content after deaerating | upper layer | 97.9% | 98.2% | 99.2% |
| | middle layer | 99.8% | 98.7% | 99.4% |

TABLE 20-continued

| Batch | | Formulation 21 | | |
|---|---|---|---|---|
| | lower layer | 99.6% | 101.2% | 99.6% |
| | mean ± RSD | 99.3% ± 1.0% | | |

The results showed that the drug suspension of formulation 21 contained uniform samples at different positions before and after deaerating, with RSD <3%.

According to Table 16 to Table 20, when the viscosity of the drug suspension ≥3,500 mPa·s, the good content uniformity can be achieved after deaerating. Preferably, the viscosity is in the range of 3,500 mPa·s to 15,000 mPa·s, and when the viscosity of the drug suspension is in this range, a good content uniformity can be achieved after deaerating. More preferably, the viscosity range was from 3,500 mPa·s to 1,0000 mPa·s, and when the viscosity of the drug suspension is in this range, a good content uniformity can be improved after deaerating.

Example 5 Accelerated Stability Experiments

Accelerated stability experiments were conducted on brexpiprazole oral soluble film prepared according to formulation 13. The results of dissolution in 0.1 M hydrochloric acid are shown below in Table 21, and all impurities and dissolution results fully meet the acceptable criteria during the acceleration period.

TABLE 21

| Sample batch number | 5 min | 15 min | 30 min |
|---|---|---|---|
| Day 0 | 31% | 55% | 64% |
| Accelerate for 1 month | 30% | 52% | 62% |
| Accelerate for 3 months | 30% | 54% | 63% |

The relevant substance standards refer to the Chinese Pharmacopoeia 2020 Edition Part IV General Rules 0512.

The relevant substance results are shown below in Table 22.

TABLE 22

| Acceleration condition (40° C., 75% RH) | Acceptable criteria | Formulation 13 |
|---|---|---|
| Day 0 | unknown impurities ≤0.5%; known impurities ≤1.0%; total impurities ≤1.5% | known impurities: ND<br>RRT = 1.44: 0.16%<br>RRT = 1.72: 0.10%<br>total impurities: 0.26% |
| Accelerate for 1 month | | known impurities: ND<br>RRT = 1.44: 0.15%<br>RRT = 1.72: 0.10%<br>total impurities: 0.25% |
| Accelerate for 3 months | | known impurities: ND<br>RRT = 1.44: 0.15%<br>RRT = 1.72: 0.08%<br>total impurities: 0.23% |

Note:
ND means not detected, RRT means relative retention time.

Example 6 Human PK Test

Pharmacokinetic experiments were performed on volunteers who were divided into 4 groups, respectively administrated brexpiprazole oral soluble films of formulation 10, formulation 12, and formulation 15, with a dosage of 2 mg; and Brexpiprazole tablets (REXULTI, 2 mg, batch number: BMS05420A, manufacturer: Otsuka Pharmaceutical Co., Ltd.), taken orally, with an oral dosage of 2 mg. Using Brexpiprazole tablets as the standard for comparison, blood was collected at 0 min before each administration and at 1 h, 2 h, 3 h, 4 h, 5 h, 6 h, 8 h, 12 h, 16 h, 24 h, 48 h, 72 h, 96 h, 120 h, 144 h, 168 h, 216 h, 312 h after each administration, respectively, and the concentrations of brexpiprazole in plasma were determined by LC-M S/MS. The results are shown below in Table 23. (h: hour; ng/ml: nanogram/milliliter; hr*ng/mL: hour*nanogram/milliliter)

TABLE 23

| Pharmacokinetic parameters | Brexpiprazole tablets | Formulation 10 | Formulation 12 | Formulation 15 |
|---|---|---|---|---|
| Average Peak Time (h) | 5.40 | 1.80 | 4.00 | 6.50 |
| Average peak concentration (ng/mL) | 75.41 | 92.55 | 77.90 | 59.90 |
| Average area under curve 0 to 72 h (hr*ng/mL) | 4,380 | 4,610 | 4,510 | 4,180 |

The average peak times of the brexpiprazole oral soluble films of formulation 10, formulation 12 and formulation 15 were 1.80 h, 4.00 h and 6.50 h, respectively, and the mean peak time for the oral tablets was 5.40 hours. The results showed that the blood concentration of brexpiprazole in vivo can be effectively controlled by controlling the active ingredient particle size and shortening the peak reaching time. When the $D_{90}$ of brexpiprazole is 9.6 μm, its peak concentration exceeded 22% of the tablets, and if the peak concentration was too high, it may cause adverse effects. When the $D_{90}$ of brexpiprazole is 60.8 μm, the peak concentration was not equivalent to the oral tablet; and when $D_{90}$=30.3 μm, the bioavailability of brexpiprazole oral soluble film can be bioequivalent to the oral tablet.

Example 7 Investigation on Ratios of Film-Forming Material and the Active Ingredient Preparation process: Brexpiprazole according to each of the formulations was slowly added to purified water, with high-speed homogenization for 30 minutes. The sample was then transferred to a stirring equipment, which was turned on. Hypromellose and polyethylene glycol were slowly added and stirred for 30 minutes. Next, the prepared coating suspension was deaerated by a vacuum centrifugal deaerator. A substrate was spreaded on a coating machine, and fixed. A scraper was adjusted to zero, and the heat temperature was set to 50-80° C. After the coating, the sample was cut to a certain size, and tested for dissolution. The usages of the components are shown below in Table 24.

TABLE 24

| Name | Formulation 22 (mg) | Formulation 23 (mg) | Formulation 24 (mg) | Formulation 25 (mg) | Note |
|---|---|---|---|---|---|
| Brexpiprazole $D_{90}$ = 37.1 μm | 2.00 | 2.00 | 2.00 | 2.00 | active ingredient |
| Hypromellose E5LV | 59.00 | 34.50 | 11.00 | 7.30 | film-forming material |
| Polyethylene glycol400 | 6.00 | 3.50 | 1.10 | 0.70 | plasticizer |
| Purified water | N/A | N/A | N/A | N/A | solvent |

Note:
Water was removed during the process and is not included in the product weight.

The dissolution results of the samples prepared by formulation described above in 0.1 M hydrochloric acid are shown below in Table 25.

TABLE 25

| Sample batch number | 5 min | 15 min | 30 min |
|---|---|---|---|
| Formulation 22 | 29% | 54% | 63% |
| Formulation 23 | 32% | 53% | 62% |
| Formulation 24 | 30% | 55% | 63% |
| Formulation 25 | 30% | 55% | 65% |

The results showed that when brexpiprazole accounts for 3% to 20%, its preparation can achieve stable and controllable dissolution.

Example 8 Investigation on Different Kinds of Film-Forming Materials

Preparation process: Brexpiprazole according to each of the formulations was slowly added to purified water, with high-speed homogenization for 30 minutes. The sample was then transferred to a stirring equipment, which was turned on. A film-forming material and a plasticizer were slowly added and stirred for 30 minutes. Next, the prepared coating suspension was deaerated by a vacuum centrifugal deaerator. A substrate was spreaded on a coating machine, and fixed. A scraper was adjusted to zero, and the heat temperature was set to 50-80° C. After the coating, the sample was cut to a certain size, and tested for dissolution. The usages of the components are shown below in Table 26, and the results of the samples prepared by formulation described above in 0.1 M hydrochloric acid are shown below in Table 27.

TABLE 26

| Name | Formulation 26 (mg) | Formulation 27 (mg) | Formulation 28 (mg) | Formulation 29 (mg) | Formulation 30 (mg) | Note |
|---|---|---|---|---|---|---|
| Brexpiprazole $D_{90}$ = 37.1 μm | 2.00 | 2.00 | 2.00 | 2.00 | 2.00 | active ingredient |
| Hydroxypropyl cellulose E5LV | 20.00 | 15.00 | N/A | 15.00 | N/A | film-forming material |
| Xanthan gum | N/A | 5.00 | 5.00 | N/A | 15.00 | film-forming material |
| Polyvinyl alcohol polyethylene glycol copolymer | N/A | N/A | 17.00 | N/A | N/A | film-forming material |

TABLE 26-continued

| Name | Formulation 26 (mg) | Formulation 27 (mg) | Formulation 28 (mg) | Formulation 29 (mg) | Formulation 30 (mg) | Note |
|---|---|---|---|---|---|---|
| Povidone K29/32 | N/A | N/A | N/A | 5.00 | 5.00 | film-forming material |
| Glycerol | 1.00 | N/A | 1.00 | N/A | 1.00 | plasticizer |
| Polysorbate 80 | N/A | 2.00 | N/A | N/A | N/A | plasticizer |
| Triethyl citrate | N/A | N/A | N/A | 2.00 | 1.00 | plasticizer |
| Purified water | 85.00 | 70.00 | 85.00 | 85.00 | 85.00 | solvent |

Note:
Water was removed during the process and not included in the product weight.

TABLE 27

| Sample batch number | 5 min | 15 min | 30 min |
|---|---|---|---|
| Formulation 26 | 30% | 54% | 63% |
| Formulation 27 | 28% | 49% | 59% |
| Formulation 28 | 29% | 55% | 62% |
| Formulation 29 | 30% | 55% | 65% |
| Formulation 30 | 27% | 51% | 60% |

The results showed that formulations 26 to 30 can achieve stable and controllable dissolution with different kinds of film-forming materials.

The technical solution of the present disclosure is not limited to the above specific examples, and any technical deformation made according to the technical solution of the present disclosure falls within the scope for protection of the present disclosure.

The invention claimed is:

1. A pharmaceutical composition for preparing an oral soluble film consisting of brexpiprazole, a film-forming material and a plasticizer, wherein the percent mass percent content of brexpiprazole in the pharmaceutical composition is 2% to 24%; and/or $D_{90}$ of brexpiprazole is: 30.3 μm≤$D_{90}$≤50 μm;

the plasticizer is polyethylene glycol;

the film-forming material is hydroxypropyl methylcellulose; and a ratio of the mass of brexpiprazole to the total mass of the film-forming material and the plasticizer is 1:(2 to 35); and the pharmaceutical composition, when formulated into a pharmaceutical suspension with water, has a viscosity of 3,500 mPa·s to 10,000 mPa·s.

2. The pharmaceutical composition according to claim 1, wherein, a ratio of the mass of brexpiprazole to the total mass of the film-forming material and the plasticizer is 1:(4 to 35); and/or a ratio of the mass of the film-forming material to the mass of the plasticizer is (5 to 20):1.

3. The pharmaceutical composition according to claim 1, wherein the pharmaceutical composition consist of: 2 parts by weight of brexpiprazole, 5 to 80 parts by weight of the film-forming material, and 0.2 to 10 parts by weight of the plasticizer.

4. A pharmaceutical suspension for preparing an oral soluble film consisting of the pharmaceutical composition according to claim 1, and water, and;

wherein a viscosity of the pharmaceutical suspension is in the range from 3,500 mPa's to 10,000 mPa: s.

5. The pharmaceutical suspension according to claim 4, wherein the pharmaceutical suspension consists of:

2 parts by weight of brexpiprazole; 5 to 80 parts by weight of the film-forming material; 0.2 to 10 parts by weight of the plasticizer; and 50 to 150 parts by weight of water.

6. A brexpiprazole oral soluble film comprising the pharmaceutical composition according to claim 1.

7. A method for preparing the brexpiprazole oral soluble film according to claim 6, comprising steps of:

(1) dispersing brexpiprazole in water, adding and mixing the film-forming material and plasticizer to obtain a pharmaceutical suspension;

(2) subjecting the pharmaceutical suspension to a deaeration treatment;

(3) preparing the film with the pharmaceutical suspension obtained in step (2).

8. The method according to claim 7, wherein in step (1), brexpiprazole is dispersed in water by high-speed homogenization for 15 to 60 minutes, and/or the film-forming material and the plasticizer are mixed for 15 to 60 minutes; and/or in step (2), a vacuum deaerator is used for the deaerating; and/or in step (3), the film is prepared at a temperature in a range from 50 to 80° C.

9. The pharmaceutical composition according to claim 1, wherein the pharmaceutical composition consists of: 2 parts by weight of brexpiprazole, 5 to 60 parts by weight of the film-forming material, and/or 0.5 to 10 parts by weight of the plasticizer.

10. The pharmaceutical suspension according to claim 4, wherein the pharmaceutical suspension consists of:

2 parts by weight of brexpiprazole; 5 to 60 parts by weight of the film-forming material; 0.5 to 10 parts by weight of the plasticizer; and 60 to 120 parts by weight of water.

11. A brexpiprazole oral soluble film, prepared by the pharmaceutical suspension according to claim 6.

* * * * *